US006850162B2

(12) United States Patent
Cacioli et al.

(10) Patent No.: US 6,850,162 B2
(45) Date of Patent: Feb. 1, 2005

(54) COMMUNICATIVE GLOVE CONTAINING EMBEDDED MICROCHIP

(75) Inventors: Paul Cacioli, Canton, OH (US); Stanley Gromelski, Canton, OH (US); Patricia Taylor, New Philadelphia, OH (US); Romeo Catracchia, Hudson, OH (US)

(73) Assignee: Ansell Healthcare Products, Inc., Massillon, OH (US)

( * ) Notice: Subject to any disclaimer, the term of this patent is extended or adjusted under 35 U.S.C. 154(b) by 0 days.

(21) Appl. No.: 09/833,900

(22) Filed: Apr. 10, 2001

(65) Prior Publication Data

US 2002/0011934 A1 Jan. 31, 2002

Related U.S. Application Data

(60) Provisional application No. 60/196,650, filed on Apr. 12, 2000.

(51) Int. Cl.[7] .............................................. G08B 23/00
(52) U.S. Cl. ................. 340/573.1; 340/572.7; 340/575; 340/576; 2/159; 2/161.6; 2/168; 2/167
(58) Field of Search .......................... 340/573.1, 571, 340/572.1, 572.7, 575, 576, 604, 540; 2/159, 161.6, 161.7, 168, 167

(56) References Cited

U.S. PATENT DOCUMENTS

| 4,910,803 A | | 3/1990 | Cukier |
| 5,114,425 A | | 5/1992 | Williams et al. |
| 5,157,379 A | | 10/1992 | Dennison |
| 5,389,097 A | * | 2/1995 | Bennett ...................... 340/540 |
| 5,562,707 A | * | 10/1996 | Prochazka et al. ............. 607/2 |
| 5,658,277 A | | 8/1997 | Marshall et al. |
| 5,734,323 A | * | 3/1998 | Hermes et al. ............. 340/540 |
| 5,976,881 A | | 11/1999 | Klingner |
| 6,016,103 A | * | 1/2000 | Leavitt ....................... 340/575 |
| 6,060,986 A | * | 5/2000 | Lederer ...................... 340/540 |
| 6,098,886 A | * | 8/2000 | Swift et al. ............ 235/472.01 |
| 6,126,572 A | * | 10/2000 | Smith ........................... 482/4 |
| 6,366,206 B1 | * | 4/2002 | Ishikawa et al. .......... 340/573.1 |

FOREIGN PATENT DOCUMENTS

GB 2303704 * 7/1995

OTHER PUBLICATIONS

Copy of International Search Report for International Application No. PCT/US01/11893.

Mike McNulty, "Award Winner, Life Saver–North Safety Engineers Develop 'Alam–Sounding' Glove", Rubber & Plastics News, Dec. 13, 1999, p. 1.

* cited by examiner

Primary Examiner—Jeffery Hofsass
Assistant Examiner—Daniel Previl
(74) Attorney, Agent, or Firm—Carton & Douglas LLP

(57) ABSTRACT

The present invention provides a communicative glove which includes means for monitoring the glove's integrity such that a breach of the glove's barrier may be detected, or in some cases anticipated, and thus a warning may be provided to the wearer of the breach.

31 Claims, 3 Drawing Sheets

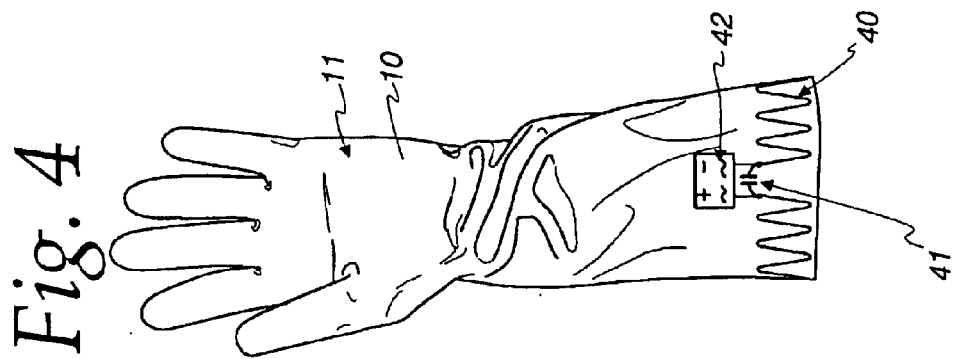

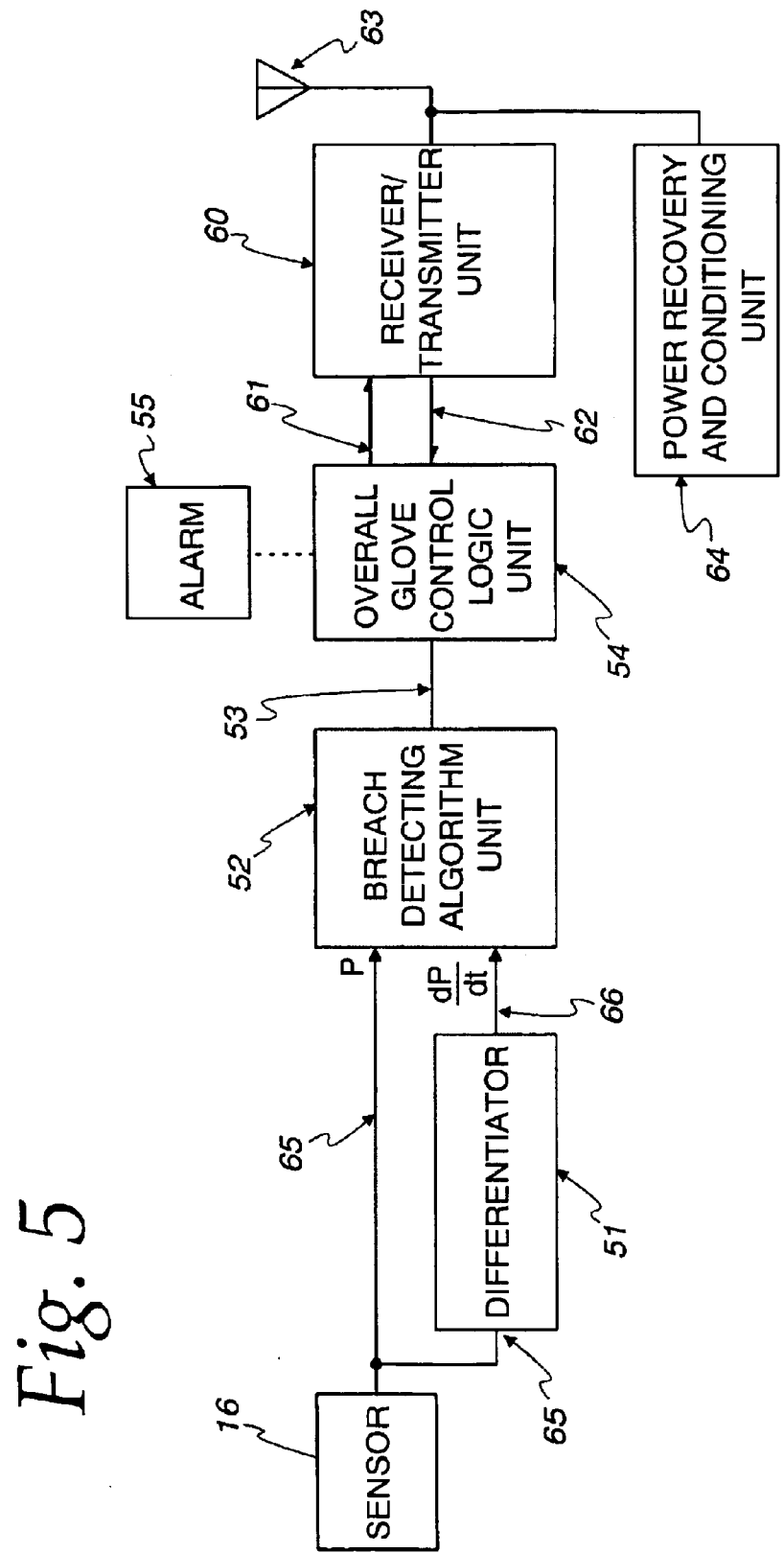

COMMUNICATIVE GLOVE CONTAINING EMBEDDED MICROCHIP

This application claims the benefit of U.S. Provisional Application No. 60/196,650, filed Apr. 12, 2000.

FIELD OF THE INVENTION

The present invention relates to a glove containing an embedded communication device. The present invention further relates to a glove that will communicate a signal to an external receiver upon breaching of the glove barrier.

BACKGROUND

Gloves, medical, surgical, industrial and the like, function principally to protect the human wearer from harm. Such protection includes protection from solid, liquid or even gaseous materials. This protection is necessary, for example, when the human wearer is handling hazardous chemicals or bodily fluids.

Glove manufacturers spend significant amounts of time and money to insure that gloves of their manufacture provide a complete and adequate barrier. Gloves are manufactured in a wide variety of types and, correspondingly, compositions. Nonetheless, a glove wearer relies on a glove to provide an adequate barrier. When a glove's barrier is breached, the wearer is then exposed to the hazard from which the glove was intended to protect the wearer.

It would therefore be an advantage to have a glove that would warn a wearer that the glove's barrier has been breached or compromised. It would be a further advantage to have a glove that would transmit a signal to an external receiver when the glove's barrier has been breached or compromised.

SUMMARY OF THE INVENTION

The present invention provides a glove having a sensor and microchip embedded in the glove. The microchip monitors the glove's integrity, in real-time, by monitoring and analyzing a signal generated by the sensor. The sensor senses one or more of several physical characteristics of the glove, each of which are indicative of the integrity or barrier making capability of the glove. In one embodiment, the glove of the present invention includes a sensor and a wire, a remote communication device can then communicate with the sensor via the wire. The wire may not only serve as an antenna, for sending and receiving data to and from the remote communication device, but the antenna may also function as a power receiver from radio or electromagnetic induction. In this embodiment, the sensor is passive in the sense that all control of the sensor resides in the remote communication device.

In another embodiment, the present invention provides a system for detecting breach of a glove. The system includes a remote communication device which sends and receives wireless communication and also acts as an electromagnetic induction source; a glove; a microchip embedded in the glove, which includes a power supply adapted to generate power from the externally applied electromagnetic induction field generated by the remote communication device; a sensor embedded in the glove which is communicatively linked to the microchip and which senses a physical characteristic of the glove, the physical characteristic being indicative of the integrity of the glove; and a wire antenna embedded in the glove, the wire antenna electronically linked to the sensor and the microchip. The wire antenna is the receiver for the externally applied electromagnetic induction field. The wire antenna can also transmit and receive a signal between the microchip and the remote communication device.

DESCRIPTION OF THE DRAWINGS

FIG. 4 illustrates a schematic of a glove of the present invention fitted with an antenna.

FIG. 5 illustrates a schematic of a preferred embodiment of control logic of the present invention.

DETAILED DESCRIPTION

Figure 1:
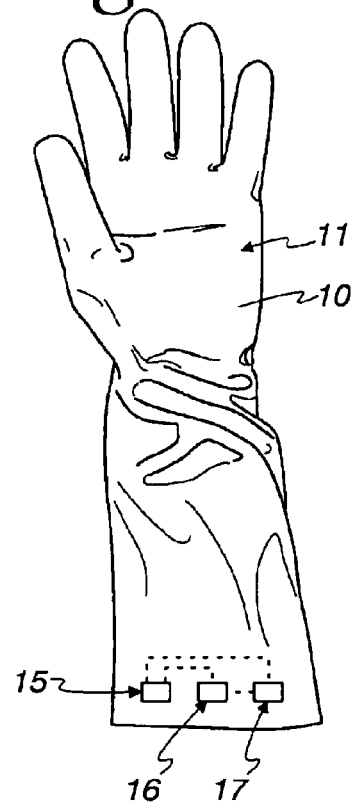
FIG. 1 illustrates a glove made according to the principles of the present invention.

A glove 10, fabricated with an electronic microchip 15 and a sensor 16 embedded in the cuff area is illustrate in FIG. 1. The glove 10 defines a barrier 11. The barrier 11 material from which the glove is made and which protects a wearer's hand from exposure to hazardous environments. The glove 10 can be manufactured from natural rubber latex or synthetic latex by, for example, a single or multiple dipping or coating process. The glove 10 may also be manufactured by a thermal molding process using natural rubber or synthetic thermoplastic elastomers, or the like. The glove 10 may be made from nitrile rubber for example. The glove 10 may be made from layers of material laminated together. The glove 10 can be powdered, powder-free, supported, unsupported, textured, untextured, disposable, or non-disposable.

The microchip 15 is a real-time monitor designed to monitor the glove's 10 integrity and sense when the barrier 11 has been breached or compromised via a signal generated by the sensor 16 and supplied to the microchip 15. Integrity, as used herein, refers to the quality of the barrier 11 and its effectiveness in protecting a wearer's hand from contact with hazardous materials. A more detailed description of the components and function of the microchip 15 is provided below. The sensor 16 may be a separate discrete transducer or in a preferred embodiment a distributed and integral part, or parts, of the glove. In one embodiment the transducer forms a layer, or layers, of a laminate from which the glove is made.

In a preferred embodiment, the microchip 15 integrally includes means for detecting changes in a signal received from the sensor 16 by appropriate sensor signal conditioning. Alternatively, the microchip 15 integrally includes a sensor as well, and thus can both detect and measure. The sensor 16 may detect any of a variety of physical parameters related to the integrity of the glove 10. For example, a piezoelectric sensor may be used to sense pressure changes at the barrier 11. Alternatively, a piezoelectric film sensor incorporated as one layer of the glove 10 may produce a voltage spike or other voltage waveform signature, or generically identifiable pattern, when physically cut or torn, for example. A suitable layered arrangement of conductive film materials separated by an insulating barrier film or material forming the sensor 16 can be monitored for integrity breaching by resistance or capacitance changes sensed by suitable electronics in the microchip 15 or a separate sensor signal conditioning microchip (not shown).

A discrete or distributed moisture sensor may be used to detect an increase in the moisture content within the barrier 11, thus indicating the barrier 11 is being compromised. Measurement, therefore, can be of extent of hydration of the barrier 11.

The signal from the discrete or distributed sensor 16, or from a combination of discrete and distributed sensor 16, may be a continuous and proportional signal, stepped, or simply irreversibly pass/fail signal, or any combination of these signal types. The signal indicates a measured, or otherwise estimated, breach indicating parameter according to the amount of change, or rate of change in one or more of the parameters being sensed.

The microchip 15, and sensor 16, whether integrated or not within the layers of the glove as a distributed sensor, or as a discrete sensor, may further include internal self test means, and, additionally a breach alarm. The alarm (not shown) could be, for example, a piezoelectric acoustic alarm device similar to a wrist watch alarm integrated into, or onto, the glove 10.

Figure 2:
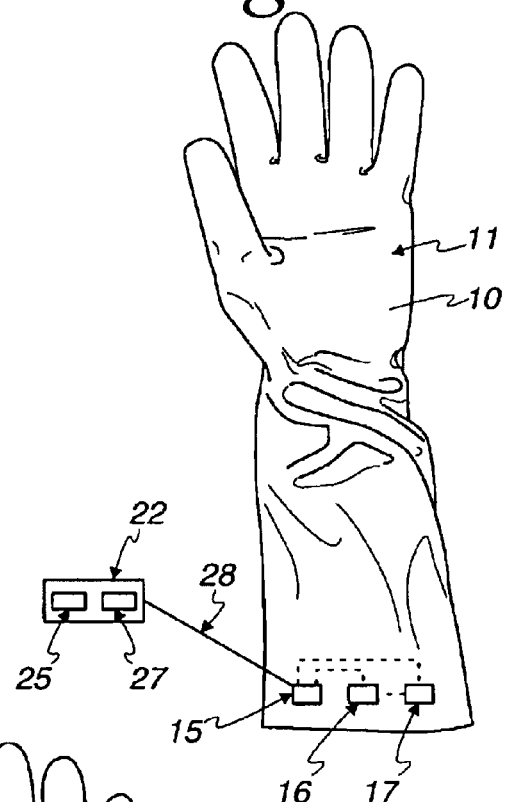
FIG. 2 illustrates a schematic of a glove and remote receiver of the present invention.

The microchip 15 may also require a power supply 17. Power supply 17 may be integral to microchip 15, or it may be external to microchip 15. Such source of electrical power may be provided by a micro-battery integrated with the glove 10, or from a capacitor charged by the action of putting on the glove 10, or from an external electromagnetic induction source or radio wave source. The power supply 17 may include a device or such parts as necessary for generating sufficient power from an externally applied electromagnetic induction field or radio signal. The power supply 17 may also power the sensor 16 (including a separate sensor signal conditioning microchip or other parts if necessary), as required. In FIGS. 1 and 2, power and signal pathways between microchip 15 and sensor 16, microchip 15 and power supply 17, and sensor 16 and power supply 17, are shown by a dashed line.

The microchip 15 is designated to monitor the signal from the sensor 16. As used herein, signal refers to an output from the sensor, which is in response to an external stimulus and is representative of a characteristic of the glove 10 or barrier 11 be sensed by the sensor 16. The signal may be representative of more than just one physical characteristic and may include multiple characteristics such as resistance and capacitance or voltage and impedance, for example. The signal may include a signal generated in response to a change in pressure, moisture, a chemical or electrical activity, or a chemical or electrical characteristic of the glove 10, and in particular, the barrier 11.

If the sensor 16 is sensing the resistance of the glove 10 or the barrier 11, stressing or puncturing of the glove 10 or barrier 11, for example, will result in a change in the resistance of the glove 10 or the barrier 11. If the sensor is sensing pressure applied to the barrier 11, for example, as the glove 10 is subjected to increasing pressure during use, the signal from the sensor 16 could be monitored so as to determine when the pressure on the barrier 11 was nearing a pressure value which could result in rupture of the barrier 11 or the glove 10. Other parameters, as described above, may thus also be sensed and used to monitor the status of the barrier 11 or glove 10 integrity.

Thus, when the glove 10 or barrier 11 is compromised or breached, the signal will change in accordance with a nominally expected response or a generic type of breach condition "signature," which can indicate that the glove's quality or effectiveness is likely to have been sufficiently or significantly degraded to enable warning or alerting the wearer of such potential or actual possible degradation. Accordingly, the microchip 15 may sense and/or monitor a change in voltage or other measurable parameter within the glove 10 or the barrier 11.

It will be understood, then, that the microchip 15 can accordingly respond to a change, or rate of change, in pressure, moisture, resistance, capacitance, electrical activity, electrical or chemical activity, or other physical parameter which may be sensed or measured and which may serve as an indicator of the glove's 10 or the barrier's 11 integrity. Rate of change information of a measured parameter may be important to allow differentiation of a false alarm from normal use signals and to allow proper identification of a signal indicative of a breached glove 10 or barrier 11 resulting from, more example, a relatively sudden puncturing or tearing the glove.

Microchip 15 preferably also include an embedded algorithm or control logic that controls the method of sensing, monitoring and alarm functions generally described above. In one embodiment, this breach sensing method may be in the form of permanent, integrated, "hard wired" analog circuitry, a digital control logic, or combination of both. The control logic part may be configured alternatively as a software routine or routines programmed onto a ROM (read only memory) component of microchip 15. In another embodiment, the embedded control logic may be in the form of a one time programmable (OTP) or re-programmable software routine or routines programmed onto an EPROM (erasable programmable read only memory) or EEPROM (electrically erasable programmable read only memory) component of microchip 15. In yet another embodiment, this control logic may be written into the microchip's random access memory (RAM) or other memory at "power up" when the glove is put on, or worm, or in the presence of a suitable power source. Alternately, an external programming device, such as a computer, may be used to write the control logic into the microchip's RAM or other memory. The control logic may be separate from the power source if desirable. Other means for providing control to microchip 15 will be understood by those of ordinary skill in the art.

Figure 3:
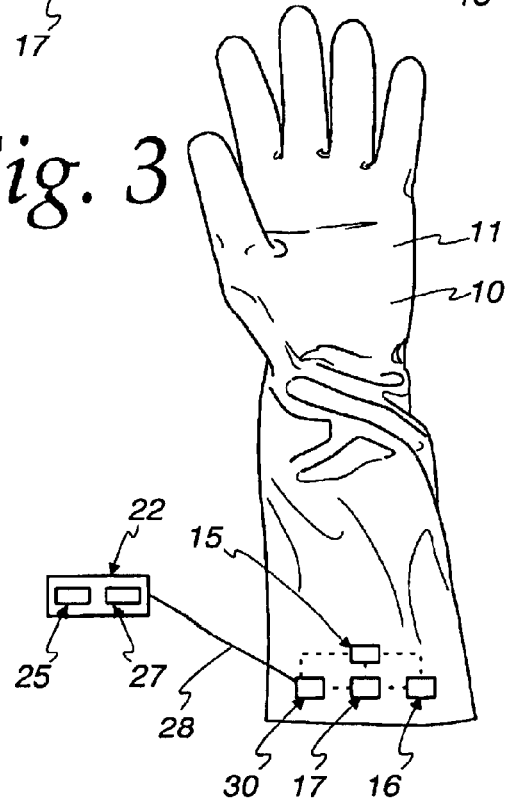
FIG. 3 illustrates a schematic of a glove and remote receiver of the present invention fitted with a separate transmitter.

Referring now to FIG. 2, the glove 10 may alternatively communicate via a wireless link and suitable communications protocol with a remote communication device 22 using the microchip 15. The remote communication device may be a receiver, a sender or both. In terms of practicality or economy, it may be preferable to have a separate microchip 30 to provide the wireless communication as illustrated in FIG. 3. The wireless communication may be unidirectional, such that only a breach alarm is communicated to an external receiver, for example. The wireless communication may be bi-directional to allow, for example, "power on programming" of the microchip 15, as described above, or to allow interrogating or reading of the sensor 16 to monitor a property of the glove 10.

If the remote communication device 22 features bi-directional communication, it can be advantageously used to tag, or uniquely identify, individual gloves 10, for example gloves 10 being used in a particular environment or by a particular wearer, or for any other purpose. Thus, it is possible to indicate to a particular wearer that his or her glove may have been, or is, potentially or actually breached or otherwise possibly degraded.

The remote communication device 22 may include a data display 25 or an alarm 27, or means to identify which glove 10, or which wearer, may have, or has had, a potential or an actual glove 10 degradation or breach. The remote communication device 22 may also include a software routine, algorithm, or other program means by which a glove 10 is uniquely identified or tagged, and a display whereby individual gloves 10 may be tagged or otherwise particularly identified to a particular wearer or site. Such tagging or identification will better facilitate glove management in potentially hazardous or other environments so indicating which glove may have been breached.

Remote communication device 22 may be located nearby, such as in the same room, to the glove 10. However, remote communication device 22 may also be located father away, in another room or centralized monitoring facility, from the glove 10. In one embodiment, microchip 15 may communicate directly with remote communication device 22 via wireless communication link 28 by incorporating such communication means "on chip," or as is illustrated in FIG. 3, the wireless communication may be via a separate transmitter or a combined transmitter/receiver microchip 30.

If the glove 10 microchip 15, or microchip 30, utilizes power up programming or receives its power supply from remote communication device 22, the remote communication device 22, or another specific remote unit, or units, for the purpose, must incorporate a radio or electromagnetic induction transmitter (not shown) for glove 10 power supply. As provide above, the remote communication device may also perform monitoring or interrogating functions with respect to the glove's 10 or barrier's 11 integrity.

FIG. 4 shows a schematic of an embodiment of the present invention wherein a thin, flexible, wire, 40, is integrated within the cuff of the glove 10 so as to enable stretching of the cuff and to allow the glove 10 to be fitted conveniently, but which wire 40 can also function as a power receiver from radio or electromagnetic induction and which wire 40 can also function as the transmitting or receiving antenna for communication purposes.

A capacitor, 41 can materially assist reception and transmission of data as well as assist more convenient delivery of power to other electrical/electronic parts as may be fitted to or within the glove as heretofore described. A rectifier 42, for example a bridge diode rectifier, is just one practical means to recover useable energy from the wire 40 or capacitor 41, if so required.

Capacitor 41 and rectifier 42 are each preferably integrated into the microchip 15, or power supply 17, or sensor 16. Capacitor 41 and rectifier 42 may be separately integrated into individual components in particular embodiments. In one embodiment capacitor 41 provides capacitance means which may be an electronically controlled capacitor, an electronically switched capacitor or a capacitance diode, facilitating wireless communication as will be known to those of ordinary skill in the art.

Such capacitance means can facilitate unidirectional or bi-directional wireless communication by modulating or switching the capacitance of the capacitor 41 with modulation of the signal to convey information as desired. This capacitance means does not necessarily significantly interfere of degrade the ability to simultaneously, or otherwise, receive glove 10 powering energy as generally described herein.

Furthermore, capacitor 41 may be all or part of the sensor 16 described above. Capacitor 41, with or without rectifier 42, is itself one possible glove breach detector which may further include the wire 40, or other conducting and communication means. In this embodiment it is preferred that the sensor 16 is formed as one or more layers of the glove, 10. Other components, such as microchip 15 and power supply 17, and others as generally described herein, may of course still be added, if desired, to provide greater features such as glove identification or improved breach detection as deemed necessary or desirable.

In one embodiment, sensor 16 may be wholly "passive" wherein the remote communication device 22 "powers" or "senses," via wireless communication, with suitable communication controls and protocols, a glove 10 breach. It will be understood, then, that the microchip 15 can still accordingly respond to a change or rate of change in pressure, moisture, resistance, capacitance, electrical activity, electrical or chemical activity or other physical parameter indicative of glove 10 or barrier 11 integrity, as describe above, but with no power supply 17 needing to be provided in or on the glove 10 itself. In this configuration, breach of the glove's 10 integrity may be measured solely by remote sensing changes in sensor 16 by the remote communication device 22. In this configuration, more complex microchip elements such as microchip 15 might be saved or microchip 15 eliminated or even all microchips eliminated. For example, a breach may change some uniquely identifiable and measurable electrical characteristic of the glove 10 or barrier 11, such as just capacitance change or impedance change and thus being detectable as described herein.

More complex changes might be accomplished by, for example, a catalyzed chemical reaction initiated by a glove 10 or barrier 11 breach altering the complex impedance of the sensor 16 so that the signal becomes sufficiently non-linear or otherwise different to be able to be measurable externally by wireless means.

Wireless communication and wireless powering of the sensor 16 and microchip 15 are likely to be designed and built to the requirements and specifications required by the particular use for a given glove type and its specific breach detection methodology or methodologies.

Wireless communications between the glove 10 and the remote communication device 22 may include use of "AIR" technology (Advanced Infrared Wireless Transmission), a short range wireless transmission limited to communication distances of about 10 meters. This technology would allow communication between a number of medical personnel wearing breach detectable gloves 10 in an operating suite for example. AIR technology is available from International Business Machines, Inc., East Fishkill, N. Y. The AIR technology device includes a transceiver, a single-chip controller, a controller macro, and a software suite. As provided by International Business Machines, Inc., the AIR controller is typically a single chip design that is also available as a VHDL ("very high speed integrated circuit hardware description language") macro for embedded platforms.

As economies of scale allow, manufacture and customization of the components of gloves 10 made according to the principles of the present invention may be tailored for particular needs. Such development is usually carried out within specialist production houses using generic technologies but with proprietary details held for that particular facility or business. As such, detailed schematic drawings of the technologies generally envisaged can only be drawn on a functional level rather than any detailed electronic schematic drawings.

FIG. 5 shows an embodiment of the present invention at a functional block-diagram level. In this embodiment, breach detection in a glove 10 incorporates many of the embodiments described above, including power up programming, programmable individual user identification, external power supply and, the use of pressure failure as a breach detection mechanism.

In FIG. 5 the breach mechanism basically depends upon a sudden loss of pressure of an otherwise entrapped gas or liquid in two separated layers of the glove caused by, for example, a tear occurring in a finger, or a slow loss of pressure caused by a small puncture. As a consequence of this breach, the entrapped gas or liquid within the separated pressure layers, leaks and results in an ultimate threshold pressure being sensed which is simply too low a pressure for an unbreached or good condition, worn, glove. Indeed, the action of the leaking gas or liquid can ameliorate the likelihood of the wearer being contaminated by a hazard external to the glove 10, as the relatively high pressure gas or liquid being forced out through the puncture hole of the glove 10 can prevent ingress of a contaminating material.

In FIG. 5, sensor 16 is a micro pressure transducer which outputs a signal, 65 (P), indicative of current glove air pressure, for example, in the inter-layer space between two nominally separated, but sealed at the cuff, layers of the glove 10. This signal, 65, is passed directly to a breach detecting algorithm unit, 52, as well as the time rate of change of pressure (dP/dt) signal, 66, calculated by a nominal differentiator, 51. Breach detecting algorithm unit, 52, considers the short term average pressure and the current and recent rate of change of pressure and estimates whether the change might be expected from normal wearing activity. If the values of these variables, or an appropriate combination of these variables, fall out of an expected normal range for the expected activity of the glove, or are just substantially out of range, from a puncture for example, then a warning can be signaled via signal path 53 to the overall glove control unit, 54. An "OK", "Fail," or "Check Glove" signal can be then propagated to a receiver/transmitter unit 60 and then onto an antenna 63. Other parts of FIG. 5, are a power recovery and conditioning unit 64 which functions as power supply 17, as provided in the description above. In a preferred embodiment, power for the glove 10 may be received via the antenna 63. The function of the power recovery and conditioning unit 64, in this preferred embodiment, is to recover sufficient energy via the antenna 63 to power the requisite electronics and sensor 16.

Signal paths 61 and 62 indicate that communication can be provided bi-directionally to the overall glove control unit 54 so to, for example, indicate to the glove 10 what its unique identification is for a particular use. This use may then be changed from time-to-time and is not construed as a "one-time-only use." A local alarm 55 may be optionally fitted to, or integrated within, the glove 10. To those of ordinary skill in the art, it will be readily appreciated that all these functions, with the exception of the alarm 55, which may be a piezo-electric sounder for example, can be wholly included within one microchip and which is, in fact likely to be so, for minimum cost, minimum size and maximum reliability.

Some of the necessary but rather auxiliary or peripheral functions of the overall glove control logic unit 54 does are control of power up, monitoring the power status for continued operation or indicate a warning, control recognition of any identification code and verify it, recognise whatever commands may be sent to the glove 10 and differentiate them from commands being transmitted to another or other gloves 10, start monitoring the glove condition after the breach detection algorithm has satisfactorily reached its "ready" mode, monitor the pressure, in this example, and its rate of change to indicate that the glove has been actually put on and is powered up, and monitor the glove 10 so that sufficient history has been determined from a wearers motions to provide base line information against which a breach or rupture is measured. As the glove is worn for longer periods of time, the base line information may be updated to allow for more sensitive measurements of glove 10 breaches.

Some of the functions one might expect the breach detection algorithm unit 52 to conduct include testing that the pressure measured is sufficient and indicates that the glove is fully on, or is properly on, or is the right size for the wearer for proper operation. The breach detection algorithm unit 52 should preferably further test that sufficient measurements have been made to establish an initial base set of measurements to be able to start delivering reliable breach status signals to the overall glove control logic unit 54.

There has been provided in accordance with the principles of the present invention, a communicative glove which assesses and reports on the status of the glove's integrity. There has also been provided in accordance with the principles of the present invention, a glove which may warn its wearer of an imminent breach of the glove barrier, thus allowing the wearer to immediately withdraw from a hazardous situation. While the invention has been described with specific embodiments and many alternatives, modifications and variations will be apparent to those skilled in the art in light of the foregoing description. Accordingly, it is intended to include all such alternatives, modifications and variations set forth within the spirit and scope of the appended claims.

What is claimed is:

1. A breach-detecting glove comprising:
   a glove, the glove made of a material;
   a fluid-filled inter-layer space between two nominally separated but sealed layers of the glove
   a microchip embedded in the material, the microchip adapted to receive a first signal, process the signal and output a second signal indicative of a barrier making capability of the glove;
   a breach-detecting sensor embedded in the material, the sensor adapted to measure a physical characteristic of the material, the physical characteristic indicative of a barrier making capability of the material, and generate the first signal, the first signal representative of the characteristic, the sensor further adapted to communicate with the microchip;
   a power supply adapted to provide power to the glove and to the sensor and
   a monitor communicatively linked with the microchip, the monitor adapted to monitor the second signal, the second signal indicative of the barrier making capability of the glove.

2. The breach-detecting communicative glove of claim 1 wherein the power supply is a battery.

3. The breach-detecting communicative glove of claim 1 wherein the power supply is a capacitance device which is charged by the action of a wearer donning the glove.

4. The breach-detecting communicative glove of claim 1 wherein the sensor is a capacitor.

5. The breach-detecting communicative glove of claim 1 wherein the sensor is a pressure transducer.

6. The breach-detecting communicative glove of claim 1 wherein the sensor senses the pressure of the fluid-filled inter-layer space.

7. The breach-detecting communicative glove of claim 6 wherein the sensor is a piezo-electric device.

8. The breach-detecting communicative glove of claim 1 wherein the sensor forms a layer of the glove.

9. The breach-detecting communicative glove of claim 8 wherein the sensor is a capacitor.

10. The breach-detecting communicative glove of claim 8 wherein the sensor is a moisture sensor.

11. The breach-detecting communicative glove of claim 1 wherein the monitor further includes an alarm.

12. The breach-detecting communicative glove of claim 1 wherein the monitor is adapted to communicate with an external remote communication device.

13. The breach-detecting communicative glove of claim 12 wherein the external remote communication device comprises an alarm.

14. The breach-detecting communicative glove of claim 1 wherein the microchip includes an embedded algorithm or control logic.

15. The breach-detecting communicative glove of claim 14 wherein the microchip is a real-time monitor.

16. The breach-detecting communicative glove of claim 1 wherein the monitor is integral to the chip.

17. A system for detecting breach of a glove, the system comprising:

a remote communication device adapted to send and receive wireless communication, the remote communication device adapted to act as an electromagnetic induction source;

a glove the glove made of a material;

a fluid-filled inter-layer space between two nominally separated but sealed layers of the glove microchip embedded in the glove, the microchip including a power supply adapted to generate power from an externally applied electromagnetic induction field, the microchip adapted to receive a first signal, process the signal and output a second signal indicative of a barrier making capability of the glove;

a breach-detecting sensor embedded in the material, the sensor adapted to measure a physical characteristic of the material and generate the first signal, the first signal representative of a physical characteristic of the glove, the physical characteristic indicative of the barrier making capability of the glove, the sensor further adapted to communicate with the microchip;

a power supply adapted to provide power to the glove and to the sensor;

a monitor communicatively linked with the microchip, the monitor adapted to monitor the second signal, the signal indicative of the barrier making capability of the glove; and a wire antenna embedded in the glove, the wire antenna electronically linked to the sensor and the microchip, the wire antenna adapted to receive an externally applied electromagnetic induction field, the wire antenna further adapted to transmit and receive a signal between the microchip and the remote communication device.

18. The system of claim 17 wherein the sensor is a capacitor.

19. The system of claim 17 wherein the sensor is a pressure transducer.

20. The system of claim 17 wherein the sensor senses the pressure of the fluid-filled inter-layer space.

21. The system of claim 20 wherein the sensor is a piezo-electric device.

22. The system of claim 17 wherein the sensor forms a layer of the glove.

23. The system of claim 22 wherein the sensor is a capacitor.

24. The system of claim 22 wherein the sensor is a moisture sensor.

25. The system of claim 17 wherein the remote communication device includes alarm.

26. The system of claim 17 wherein the remote communication device includes a data display.

27. The system of claim 26 wherein the data display indicates the status of the integrity of the glove.

28. A system for detecting breach of a glove, the system comprising:

a remote communication device adapted to send and receive wireless communication, the remote communication device adapted to act as an electromagnetic induction source;

a glove, the glove made of a material;

a fluid-filled inter-layer space between two nominally separated but sealed layers of the glove;

a breach-detecting sensor embedded in the material, the sensor adapted to measure a physical characteristic of the material, the physical characteristic indicative of a barrier making capability of the glove, the sensor adapted to generate power from an externally applied electromagnetic induction field, the sensor further adapted to be monitored by the remote communication device; and a wire antenna embedded in the glove, the wire antenna electronically linked to the sensor, the wire antenna adapted to receive an externally applied electromagnetic induction field, the wire antenna further adapted to transmit and receive a signal between the sensor and the remote communication device.

29. The system of claim 28 wherein the sensor is a capacitor.

30. The system of claim 28 wherein the remote communication device includes a data display.

31. The system of claim 30 wherein the data display indicates the status of the integrity of the glove.

* * * * *